(12) United States Patent
Roux et al.

(10) Patent No.: US 8,114,605 B1
(45) Date of Patent: Feb. 14, 2012

(54) DIAGNOSTIC TEST FOR DETECTING ANTI-CASHEW IGE IN PATIENTS

(75) Inventors: Kenneth H. Roux, Tallahassee, FL (US); Shridhar K. Sathe, Tallahassee, FL (US); Suzanne S. Teuber, Davis, CA (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 12/025,875

(22) Filed: Feb. 5, 2008

Related U.S. Application Data

(60) Division of application No. 11/096,910, filed on Apr. 1, 2005, now Pat. No. 7,381,534, which is a continuation of application No. 10/264,303, filed on Oct. 3, 2002, now Pat. No. 6,884,877.

(60) Provisional application No. 60/326,793, filed on Oct. 3, 2001, provisional application No. 60/371,774, filed on Apr. 11, 2002.

(51) Int. Cl.
*G01N 33/53* (2006.01)

(52) U.S. Cl. ...................................... 435/7.1

(58) Field of Classification Search .................. None
See application file for complete search history.

(56) References Cited

PUBLICATIONS

Blumenthal et al. 'Definition of an Allergen.' Allergens and Allergen Immunotherapy. Ed. R Lockey, S. Bukantz and J. Bousquet. New York: Marcel Decker, 2004. 37-50.*
Lerner et al. 'Tapping the immunological repertoire to produce antibodies of predetermined specificity.' Nature. 299:592-596, 1982.*
Funes et al. 'Allergy to Anacadiaceae. Identification of allergens.' Allergol. Immunol. Clin 14(2):82-89, 1999.*

* cited by examiner

*Primary Examiner* — Nora Rooney
(74) *Attorney, Agent, or Firm* — Allen, Dyer, Doppelt, Milbrath & Gilchrist, P.A.

(57) ABSTRACT

Disclosed are major allergenic proteins in cashew nut, which are legumin-like proteins and 2S albumins. Also disclosed is a polypeptide allergen in the 7S superfamily, which includes vicilin-like and sucrose binding proteins. Several linear epitopes of the cashew nut are identified and characterized. The invention further discloses the sequence of cDNA encoding the allergenic polypeptide, the allergen being designated Ana o 1, and also describes the characterization of the expressed recombinant polypeptide and associated methods employing the polypeptide.

1 Claim, 3 Drawing Sheets

A
```
Aol.1   GCCATAATGGGTCCGCCTACAAAGTTTTCTTTTTCTCTTTTTCTCGTTTCTGTTTTGGTCCTGTGTTTAGGTTTTGCTTT    80
Aol.2   ................................................................................

Aol.1,2 GGCTAAAATAGACCCGGAGCTGAAACAGTGCAAGCACCAGTGCAAAGTCCAGAGGCAGTATCACGAGCAACAGAAGGAGC   160
Aol.1,2 AGTGTGTGAAAGAGTGTGAAAAGTACTACAAAGAGAAGAAAGGACGGGAACGAGAGCATGAGGAGGAAGAAGAAGAATGG   240
Aol.1,2 GGAACTGGTGGCGTTGATGAACCCAGCACTCATGAACCAGCTGAAAAGCATCTCAGTCAGTGCATGAGGCAGTGCGAGAG   320
Aol.1,2 ACAAGAAGGAGGACAACAAAAGCAACTATGCCGCTTTAGGTGTCAGGAGAGGTATAAGAAAGAGAGAGGACAACATAATT   400
Aol.1,2 ACAAGAGAGAAGACGATGAAGACGAAGACGAAGACGAAGCCGAGGAAGAAGATGAGAATCCCTATGTATTCGAAGACGAA   480
Aol.1,2 GATTTCACCACCAAAGTCAAGACTGAGCAAGGAAAAGTTGTTCTTCTTCCCAAGTTCACTCAAAAATCGAAGCTTCTTCA   560
Aol.1,2 TGCCCTGGAGAAATACCGTCTAGCCGTTCTCGTTGCGAATCCTCAGGCTTTTGTAGTTCCAAGCCACATGGATGCTGACA   640
Aol.1,2 GTATTTTCTTCGTTTCTTGGGGACGAGGAACGATCACCAAGATCCTTGAGAACAAACGAGAGAGCATTAATGTCAGACAG   720
Aol.1,2 GGAGACATCGTCAGCATTAGTTCTGGTACTCCTTTTTATATCGCCAATAACGACGAAAACGAGAAGCTTTACCTCGTCCA   800
Aol.1,2 ATTCCTCCGACCAGTCAATCTTCCAGGGCATTTCGAAGTGTTTCATGGACCAGGCGGTGAAAATCCAGAGTCTTTCTACA   880
Aol.1,2 GAGCTTTCAGCTGGGAAATACTAGAAGCCGCACTGAAGACCTCAAAGGACACACTTGAGAAACTTTTCGAGAAACAGGAC   960

Aol.1   CAAGGAACTATCATGAAAGCCTCCAAAGAACAAATTCGGGCTATGAGCCGGAGAGGCGAAGGCCCTAAAATTTGGCCATT  1040
Aol.2   ....................................G...........................................

Aol.1,2 TACAGAGGAATCAACGGGATCATTCAAACTTTTCAAAAAGGATCCCTCTCAATCCAATAAATACGGCCAACTCTTTGAAG  1120
Aol.1,2 CTGAACGTATAGATTATCCGCCGCTTGAAAAGCTTGACATGGTTGTCTCCTACGCGAACATCACCAAGGGAGGAATGTCT  1200
Aol.1,2 GTTCCATTCTACAACTCACGGGCAACGAAAATAGCCATTGTTGTTTCAGGAGAAGGATGCGTTGAAATAGCGTGTCCTCA  1280
Aol.1,2 TCTATCCTCTTCGAAAAGCTCACACCCAAGTTACAAGAAATTGAGGGCACGGATAAGAAAGGACACAGTGTTCATTGTCC  1360
Aol.1,2 CGGCGGGTCACCCTTTCGCGACTGTTGCTTCGGGAAATGAAAACTTGGAAATCGTGTGCTTTGAAGTAAACGCAGAAGGC  1440
Aol.1,2 AACATAAGGTACACACTTGCGGGGAAGAAGAACATTATAAAGGTCATGGAGAAGGAAGCGAAAGAGTTGGCATTCAAAAT  1520
Aol.1,2 GGAAGGAGAAGAAGTGGACAAAGTGTTTGGAAAACAAGATGAAGAGTTTTTCTTCCAGGGGCCGGAATGGCGAAAGGAAA  1600

Aol.1   AAGAAGGGCGTGCTGATGAATGAGAAGAAATGGGAAGGTTGTTTGGGGTCTGAGAAAGGCTGAGCTACTGACTAGTGAAC  1680
Aol.2   ....................................................................

Aol.1   GTTATATATGGATAACGTATATATGTATGTAAATGTGAGCAGCGGACATCATCTTCCCAACTGCATTAAGCAAAACTAAA  1760

Aol.1   TAAAAAGAAAAGGCTTTAGCCAAAAAAAAAAAAAAAAAAAAAAAAAAAAAA                                1810
```

B
```
                    ^Ana o 1a
Aol.1   AIMGPPTKFSFSLFLVSVLVLCLGFALAKIDPELKQCKHQCKVQRQYDEQQKEQCVKECEKYYKEKKGREREHEEEEEEW   80
Aol.2   ................................................................................

^Ana o 1b
Aol.1,2 GTGGVDEPSTHEPAEKHLSQCMRQCERQEGGQQKQLCRFRCQERYKKERGQHNYKREDDEDEDEDEAEEEDENPYVFEDE  160
Aol.1,2 DFTTKVKTEQGKVVLLPKFTQKSKLLHALEKYRLAVLVANPQAFVVPSHMDADSIFFVSWGRGTITKILENKRESINVRQ  240
Aol.1,2 GDIVSISSGTPFYIANNDENEKLYLVQFLRPVNLPGHFEVFHGPGGENPESFYRAFSWEILEAALKTSKDTLEKLFEKQD  320

Aol.1   QGTIMKASKEQIRAMSRRGEGPKIWPFTEESTGSFKLFKKDPSQSNKYGQLFEAERIDYPPLEKLDMVVSYANITKGGMS  400
Aol.2   ...........V....................................................................

Aol.1,2 VPFYNSRATKIAIVVSGEGCVEIACPHLSSSKSSHPSYKKLRARIRKDTVFIVPAGHPFATVASGNENLEIVCFEVNAEG  480
Aol.1,2 NIRYTLAGKKNIIKVMEKEAKELAFKMEGEEVDKVFGKQDEEFFFQGPEWRKEKEGRADE                      540
```

FIG. 1

SEQUENCE LISTING

```
<160> NUMBER OF SEQ ID NOS: 15

<210> SEQ ID NO 1
<211> LENGTH: 1730
<212> TYPE: DNA
<213> ORGANISM: Anacardium occidental

<400> SEQUENCE: 1
gccataatgg gtccgcctac aaagttttct ttttctcttt ttctcgtttc tgttttggtc      60
ctgtgtttag gttttgcttt agtgtgtgaa agagtgtgaa aagtactaca aagagaagaa     120
aggacgggaa cgagagcatg aggaggaaga agaagaatgg ggaactggtg gcgttgatga     180
acccagcact catgaaccag ctgaaaagca tctcagtcag tgcatgaggc agtgcgagag     240
acaagaagga ggacaacaaa agcaactatg ccgctttagg tgtcaggaga ggtataagaa     300
agagagagga caacataatt acaagagaga agacgatgaa gacgaagacg aagacgaagc     360
cgaggaagaa gatgagaatc cctatgtatt cgaagacgaa gatttcacca ccaaagtcaa     420
gactgagcaa ggaaaagttg ttcttcttcc caagttcact caaaaatcga agcttcttca     480
tgccctggag aaataccgtc tagccgttct cgttgcgaat cctcaggctt ttgtagttcc     540
aagccacatg gatgctgaca gtattttctt cgtttcttgg ggacgaggaa cgatcaccaa     600
gatccttgag aacaaacgag agagcattaa tgtcagacag ggagacatcg tcagcattag     660
ttctggtact ccttttata tcgccaataa cgacgaaaac gagaagcttt acctcgtcca     720
attcctccga ccagtcaatc ttccagggca tttcgaagtg tttcatggac caggcggtga     780
aaatccagag tcttttctaca gagctttcag ctgggaaata ctagaagccg cactgaagac     840
ctcaaaggac acacttgaga aacttttcga gaaacaggac caaggaacta tcatgaaagc     900
ctccaaagaa caaattcggg ctatgagccg gagaggcgaa ggccctaaaa tttggccatt     960
tacagaggaa tcaacgggat cattcaaact tttcaaaaag gatccctctc aatccaataa    1020
atacggccaa ctctttgaag ctgaacgtat agattatccg ccgcttgaaa agcttgacat    1080
ggttgtctcc tacgcgaaca tcaccaaggg aggaatgtct gttccattct acaactcacg    1140
ggcaacgaaa atagccattg ttgtttcagg agaaggatgc gttgaaatag cgtgtcctca    1200
tctatcctct tcgaaaagct cacacccaag ttacaagaaa ttgagggcac ggataagaaa    1260
ggacacagtg ttcattgtcc cggcgggtca cccttttcgcg actgttgctt cgggaaatga    1320
aaacttggaa atcgtgtgct ttgaagtaaa cgcagaaggc aacataaggt acacacttgc    1380
ggggaagaag aacattataa aggtcatgga gaaggaagcc aaagagttgg cattcaaaat    1440
ggaaggagaa gaagtggaca aagtgtttgg aaaacaagat gaagagtttt tcttccaggg    1500
gccggaatgg cgaaaggaaa aagaagggcg tgctgatgaa tgagaagaaa tgggaaggtt    1560
gtttggggtc tgagaaaggc tgagctactg actagtgaac gttatatatg gataacgtat    1620
```

```
atatgtatgt aaatgtgagc agcggacatc atcttcccaa ctgcattaag caaaactaaa    1680
taaaagaaa aggctttagc caaaaaaaaa aaaaaaaaaa aaaaaaaaaa                1730
```

<210> SEQ ID NO 2
<211> LENGTH: 1660
<212> TYPE: DNA
<213> ORGANISM: Anacardium occidental

<400> SEQUENCE: 2

```
ccgcctacaa agtttctttt ttctcttttt ctcgtttctg ttttggtcct gtgtttaggt      60
tttgctttgg ctaaaataga cccggagctg aaacagtgca agcaccagtg caaagtccag     120
aggcagtatg acgagcaaca gaaggagcag tgtgtgaaag agtgtgaaaa gtactacaaa     180
gagaagaaag gacgggaacg agagcatgag gaggaagaag aagaatgggg aactggtggc     240
gttgatgaac ccagcactca tgaaccagct gaaaagcatc tcagtcagtg catgaggcag     300
tgcgagagac aagaaggagg acaacaaaag caactatgcc gctttaggtg tcaggagagg     360
tataagaaag agagaggaca acataattac aagagagaag acgatgaaga cgaagacgaa     420
gacgaagccg aggaagaaga tgagaatccc tatgtattcg aagacgaaga tttcaccacc     480
aaagtcaaga ctgagcaagg aaaagttgtt cttcttccca agttcactca aaaatcgaag     540
cttcttcatg ccctggagaa ataccgtcta gccgttctcg ttgcgaatcc tcaggctttt     600
gtagttccaa gccacatgga tgctgacagt attttcttcg tttcttgggg acgaggaacg     660
atcaccaaga tccttgagaa caaacgagag agcattaatg tcagacaggg agacatcgtc     720
agcattagtt ctggtactcc ttttatatc gccaataacg acgaaaacga aagctttac      780
ctcgtccaat cctccgacc agtcaatctt ccagggcatt tcgaagtgtt tcatggacca     840
ggcggtgaaa atccagagtc tttctacaga gctttcagct gggaaatact agaagccgca     900
ctgaagacct caaaggacac acttgagaaa cttttcgaga acaggacca aggaactatc     960
atgaaagcct ccaaagaaca agttcgggct atgagccgga gaggcgaagg ccctaaaatt    1020
tggccattta cagaggaatc aacgggatca ttcaaacttt tcaaaaagga tccctctcaa    1080
tccaataaat acggccaact ctttgaagct gaacgtatag attatccgcc gcttgaaaag    1140
cttgacatgg ttgtctccta cgcgaacatc accaagggag gaatgtctgt tccattctac    1200
aactcacggg caacgaaaat agccattgtt gtttcaggag aaggatgcgt tgaaatagcg    1260
tgtcctcatc tatcctcttc gaaaagctca cacccaagtt acaagaaatt gagggcacgg    1320
ataagaaagg acacagtgtt cattgtcccg gcgggtcacc ctttcgcgac tgttgcttcg    1380
ggaaatgaaa acttggaaat cgtgtgcttt gaagtaaacg cagaaggcaa cataaggtac    1440
acacttgcgg ggaagaagaa cattataaag gtcatggaga aggaagcgaa agagttggca    1500
ttcaaaatgg aaggagaaga agtggacaaa gtgtttggaa aacaagatga agagtttttc    1560
ttccagggcc cggaatggcg aaaggaaaaa gaagggcgtg ctgatgaatg agaagaaatg    1620
ggaaggttgt ttggggtctg agaaaggctg agctactgac                          1660
```

<210> SEQ ID NO 3
<211> LENGTH: 540
<212> TYPE: PRT
<213> ORGANISM: Anacardium occidental

<400> SEQUENCE: 3

```
Ala Ile Met Gly Pro Pro Thr Lys Phe Ser Phe Ser Leu Phe Leu Val
1               5                   10                  15

Ser Val Leu Val Leu Cys Leu Gly Phe Ala Leu Ala Lys Ile Asp Pro
```

```
            20                  25                  30
Glu Leu Lys Gln Cys Lys His Gln Cys Lys Val Gln Arg Gln Tyr Asp
            35                  40                  45

Glu Gln Gln Lys Glu Gln Cys Val Lys Glu Cys Glu Lys Tyr Tyr Lys
            50                  55                  60

Glu Lys Lys Gly Arg Glu Arg Glu His Glu Glu Glu Glu Glu Glu Trp
65                  70                  75                  80

Gly Thr Gly Gly Val Asp Glu Pro Ser Thr His Glu Pro Ala Glu Lys
                    85                  90                  95

His Leu Ser Gln Cys Met Arg Gln Cys Glu Arg Gln Glu Gly Gly Gln
                100                 105                 110

Gln Lys Gln Leu Cys Arg Phe Arg Cys Gln Glu Arg Tyr Lys Lys Glu
            115                 120                 125

Arg Gly Gln His Asn Tyr Lys Arg Glu Asp Glu Asp Glu Asp Glu
            130                 135                 140

Asp Glu Ala Glu Glu Asp Glu Asn Pro Tyr Val Phe Glu Asp Glu
145                 150                 155                 160

Asp Phe Thr Thr Lys Val Lys Thr Glu Gln Gly Lys Val Val Leu Leu
                165                 170                 175

Pro Lys Phe Thr Gln Lys Ser Lys Leu Leu His Ala Leu Glu Lys Tyr
                180                 185                 190

Arg Leu Ala Val Leu Val Ala Asn Pro Gln Ala Phe Val Pro Ser
            195                 200                 205

His Met Asp Ala Asp Ser Ile Phe Phe Val Ser Trp Gly Arg Gly Thr
            210                 215                 220

Ile Thr Lys Ile Leu Glu Asn Lys Arg Glu Ser Ile Asn Val Arg Gln
225                 230                 235                 240

Gly Asp Ile Val Ser Ile Ser Gly Thr Pro Phe Tyr Ile Ala Asn
                245                 250                 255

Asn Asp Glu Asn Glu Lys Leu Tyr Leu Val Gln Phe Leu Arg Pro Val
            260                 265                 270

Asn Leu Pro Gly His Phe Glu Val Phe His Gly Pro Gly Glu Asn
            275                 280                 285

Pro Glu Ser Phe Tyr Arg Ala Phe Ser Trp Glu Ile Leu Glu Ala Ala
            290                 295                 300

Leu Lys Thr Ser Lys Asp Thr Leu Glu Lys Leu Phe Glu Lys Gln Asp
305                 310                 315                 320

Gln Gly Thr Ile Met Lys Ala Ser Lys Glu Gln Ile Arg Ala Met Ser
                325                 330                 335

Arg Arg Gly Glu Gly Pro Lys Ile Trp Pro Phe Thr Glu Glu Ser Thr
            340                 345                 350

Gly Ser Phe Lys Leu Phe Lys Lys Asp Pro Ser Gln Ser Asn Lys Tyr
            355                 360                 365

Gly Gln Leu Phe Glu Ala Glu Arg Ile Asp Tyr Pro Pro Leu Glu Lys
            370                 375                 380

Leu Asp Met Val Val Ser Tyr Ala Asn Ile Thr Lys Gly Gly Met Ser
385                 390                 395                 400

Val Pro Phe Tyr Asn Ser Arg Ala Thr Lys Ile Ala Ile Val Val Ser
                405                 410                 415

Gly Glu Gly Cys Val Glu Ile Ala Cys Pro His Leu Ser Ser Ser Lys
                420                 425                 430

Ser Ser His Pro Ser Tyr Lys Lys Leu Arg Ala Arg Ile Arg Lys Asp
            435                 440                 445
```

```
Thr Val Phe Ile Val Pro Ala Gly His Pro Phe Ala Thr Val Ala Ser
    450                 455                 460

Gly Asn Glu Asn Leu Glu Ile Val Cys Phe Glu Val Asn Ala Glu Gly
465                 470                 475                 480

Asn Ile Arg Tyr Thr Leu Ala Gly Lys Lys Asn Ile Ile Lys Val Met
                485                 490                 495

Glu Lys Glu Ala Lys Glu Leu Ala Phe Lys Met Glu Gly Glu Glu Val
                500                 505                 510

Asp Lys Val Phe Gly Lys Gln Asp Glu Glu Phe Phe Phe Gln Gly Pro
                515                 520                 525

Glu Trp Arg Lys Glu Lys Glu Arg Ala Asp Glu
530                 535                 540

<210> SEQ ID NO 4
<211> LENGTH: 536
<212> TYPE: PRT
<213> ORGANISM: Anacardium occidental

<400> SEQUENCE: 4

Pro Pro Thr Lys Phe Ser Phe Ser Leu Phe Leu Val Ser Val Leu Val
1               5                   10                  15

Leu Cys Leu Gly Phe Ala Leu Ala Lys Ile Asp Pro Glu Leu Lys Gln
                20                  25                  30

Cys Lys His Gln Cys Lys Val Gln Arg Gln Tyr Asp Glu Gln Gln Lys
                35                  40                  45

Glu Gln Cys Val Lys Glu Cys Glu Lys Tyr Tyr Lys Glu Lys Lys Gly
            50                  55                  60

Arg Glu Arg Glu His Glu Glu Glu Glu Trp Gly Thr Gly Gly
65                  70                  75                  80

Val Asp Glu Pro Ser Thr His Glu Pro Ala Glu Lys His Leu Ser Gln
                85                  90                  95

Cys Met Arg Gln Cys Glu Arg Gln Glu Gly Gln Gln Lys Gln Leu
                100                 105                 110

Cys Arg Phe Arg Cys Gln Glu Arg Tyr Lys Lys Glu Arg Gly Gln His
                115                 120                 125

Asn Tyr Lys Arg Glu Asp Asp Glu Asp Glu Asp Glu Ala Glu
    130                 135                 140

Glu Glu Asp Glu Asn Pro Tyr Val Phe Glu Asp Glu Asp Phe Thr Thr
145                 150                 155                 160

Lys Val Lys Thr Glu Gln Gly Lys Val Val Leu Leu Pro Lys Phe Thr
                165                 170                 175

Gln Lys Ser Lys Leu Leu His Ala Leu Glu Lys Tyr Arg Leu Ala Val
                180                 185                 190

Leu Val Ala Asn Pro Gln Ala Phe Val Val Pro Ser His Met Asp Ala
    195                 200                 205

Asp Ser Ile Phe Phe Val Ser Trp Gly Arg Gly Thr Ile Thr Lys Ile
    210                 215                 220

Leu Glu Asn Lys Arg Glu Ser Ile Asn Val Arg Gln Gly Asp Ile Val
225                 230                 235                 240

Ser Ile Ser Ser Gly Thr Pro Phe Tyr Ile Ala Asn Asn Asp Glu Asn
                245                 250                 255

Glu Lys Leu Tyr Leu Val Gln Phe Leu Arg Pro Val Asn Leu Pro Gly
                260                 265                 270

His Phe Glu Val Phe His Gly Pro Gly Gly Glu Asn Pro Glu Ser Phe
    275                 280                 285
```

```
Tyr Arg Ala Phe Ser Trp Glu Ile Leu Glu Ala Ala Leu Lys Thr Ser
    290                 295                 300

Lys Asp Thr Leu Glu Lys Leu Phe Glu Lys Gln Asp Gln Gly Thr Ile
305                 310                 315                 320

Met Lys Ala Ser Lys Glu Gln Val Arg Ala Met Ser Arg Arg Gly Glu
                325                 330                 335

Gly Pro Lys Ile Trp Pro Phe Thr Glu Glu Ser Thr Gly Ser Phe Lys
            340                 345                 350

Leu Phe Lys Lys Asp Pro Ser Gln Ser Asn Lys Tyr Gly Gln Leu Phe
        355                 360                 365

Glu Ala Glu Arg Ile Asp Tyr Pro Pro Leu Glu Lys Leu Asp Met Val
370                 375                 380

Val Ser Tyr Ala Asn Ile Thr Lys Gly Gly Met Ser Val Pro Phe Tyr
385                 390                 395                 400

Asn Ser Arg Ala Thr Lys Ile Ala Ile Val Val Ser Gly Glu Gly Cys
                405                 410                 415

Val Glu Ile Ala Cys Pro His Leu Ser Ser Lys Ser Ser His Pro
            420                 425                 430

Ser Tyr Lys Lys Leu Arg Ala Arg Ile Arg Lys Asp Thr Val Phe Ile
        435                 440                 445

Val Pro Ala Gly His Pro Phe Ala Thr Val Ala Ser Gly Asn Glu Asn
450                 455                 460

Leu Glu Ile Val Cys Phe Glu Val Asn Ala Glu Gly Asn Ile Arg Tyr
465                 470                 475                 480

Thr Leu Ala Gly Lys Lys Asn Ile Ile Lys Val Met Glu Lys Glu Ala
                485                 490                 495

Lys Glu Leu Ala Phe Lys Met Glu Gly Glu Val Asp Lys Val Phe
            500                 505                 510

Gly Lys Gln Asp Glu Glu Phe Phe Gln Gly Pro Glu Trp Arg Lys
        515                 520                 525

Glu Lys Glu Gly Arg Ala Asp Glu
    530                 535

<210> SEQ ID NO 5
<211> LENGTH: 15
<212> TYPE: PRT
<213> ORGANISM: Anacardium occidental

<400> SEQUENCE: 5

Ala Ile Met Gly Pro Pro Thr Lys Phe Ser Phe Ser Leu Phe Leu
1               5                   10                  15

<210> SEQ ID NO 6
<211> LENGTH: 15
<212> TYPE: PRT
<213> ORGANISM: Anacardium occidental

<400> SEQUENCE: 6

Cys Lys Val Gln Arg Gln Tyr Asp Glu Gln Gln Lys Glu Gln Cys
1               5                   10                  15

<210> SEQ ID NO 7
<211> LENGTH: 15
<212> TYPE: PRT
<213> ORGANISM: Anacardium occidental

<400> SEQUENCE: 7

Glu Gln Gln Lys Glu Gln Cys Val Lys Glu Cys Glu Lys Tyr Tyr
1               5                   10                  15
```

```
<210> SEQ ID NO 8
<211> LENGTH: 15
<212> TYPE: PRT
<213> ORGANISM: Anacardium occidental

<400> SEQUENCE: 8

Lys Glu Cys Glu Lys Tyr Tyr Lys Glu Lys Lys Gly Arg Glu Arg
1               5                   10                  15

<210> SEQ ID NO 9
<211> LENGTH: 15
<212> TYPE: PRT
<213> ORGANISM: Anacardium occidental

<400> SEQUENCE: 9

Glu Lys Lys Gly Arg Glu Arg Glu His Glu Glu Glu Glu Glu Glu
1               5                   10                  15

<210> SEQ ID NO 10
<211> LENGTH: 15
<212> TYPE: PRT
<213> ORGANISM: Anacardium occidental

<400> SEQUENCE: 10

Asp Glu Ala Glu Glu Glu Asp Glu Asn Pro Tyr Val Phe Glu Asp
1               5                   10                  15

<210> SEQ ID NO 11
<211> LENGTH: 15
<212> TYPE: PRT
<213> ORGANISM: Anacardium occidental

<400> SEQUENCE: 11

Arg Arg Gly Glu Gly Pro Lys Ile Trp Pro Phe Thr Glu Glu Ser
1               5                   10                  15

<210> SEQ ID NO 12
<211> LENGTH: 15
<212> TYPE: PRT
<213> ORGANISM: Anacardium occidental

<400> SEQUENCE: 12

Asn Ile Thr Lys Gly Gly Met Ser Val Pro Phe Tyr Asn Ser Arg
1               5                   10                  15

<210> SEQ ID NO 13
<211> LENGTH: 15
<212> TYPE: PRT
<213> ORGANISM: Anacardium occidental

<400> SEQUENCE: 13

Thr Lys Ile Ala Ile Val Val Ser Gly Glu Gly Cys Val Glu Ile
1               5                   10                  15

<210> SEQ ID NO 14
<211> LENGTH: 15
<212> TYPE: PRT
<213> ORGANISM: Anacardium occidental

<400> SEQUENCE: 14

Ser Ser His Pro Ser Tyr Lys Lys Leu Arg Ala Arg Ile Arg Lys
1               5                   10                  15

<210> SEQ ID NO 15
```

```
<211> LENGTH: 15
<212> TYPE: PRT
<213> ORGANISM: Anacardium occidental

<400> SEQUENCE: 15

Glu Glu Phe Phe Phe Gln Gly Pro Glu Trp Arg Lys Glu Lys Glu
1               5                   10                  15
```

DIAGNOSTIC TEST FOR DETECTING ANTI-CASHEW IGE IN PATIENTS

RELATED APPLICATION

This application is a division of and claims priority from utility patent application Ser. No. 11/096,910 filed 1 Apr. 2005, now U.S. Pat. No. 7,381,534, which claimed priority from and was a continuation of Ser. No. 10/264,303, filed on Oct. 3, 2002, now U.S. Pat. No. 6,884,877, and which claimed priority from provisional application Ser. No. 60/326,793, filed on Oct. 3, 2001, and Ser. No. 60/371,774, filed on Apr. 11, 2002, each priority application being incorporated herein by reference in its entirety.

SEQUENCE LISTING

This application includes a "Sequence Listing" printed on paper and a copy thereof in computer readable format (CRF copy) submitted on a Compact Disk-Recordable (CD-R) containing one file named 12025875-SEQS.ST25, which is 16 KB in size and was recorded on 10 Jun. 2009, which CRF copy is incorporated herein by reference in its entirety.

FIELD OF THE INVENTION

The present invention relates to the field of allergies to nuts and, more particularly, to purified linear epitope polypeptides from cashews, nucleic acids encoding therefor, and associated methods.

BACKGROUND OF THE INVENTION

It is estimated that up to 8% of children less than 3 years of age and 2% of adults are affected by food allergies. While food-induced allergic reactions are the most common cause of outpatient anaphylaxis, the majority of severe reactions of this kind are caused by peanuts and tree nuts. Most plant food allergens can be found among pathogenesis-related proteins, seed storage albumins and globulins, and a-amylase and protease inhibitors.

Cashew nuts have been associated with contact or systemic dermatitis (to cardol and anacardic acid found in the cashew nut shell oil[1]), atopic dermatitis, and IgE-mediated systemic allergic reactions.[2-4] Pistachios are another allergenic member of the Anacardiaceae family and show extensive in vitro cross-reactivity with cashews.[5,6] Cashew nuts are widely used in snack foods and as an ingredient in a variety of processed foods such as bakery and confectionery products.

By sequencing of the N-termini and selected internal digests, we have found that the major allergenic proteins in cashew nut are legumin-like proteins and 2S albumins. We have also identified a polypeptide allergen in the 7S superfamily, which includes vicilin-like and sucrose binding proteins. Herein, we disclose the sequence of a cDNA encoding this allergenic polypeptide, designated Ana o 1, and describe the characterization of the expressed recombinant polypeptide. In addition, we identify several linear epitopes and compare these to the allergenic peanut vicilin, Ara h 1.[7]

REFERENCES CITED

1. Marks J G Jr, DeMelfi T, McCarthy M A, Witte E J, Castagnoli N, Epstein WL, Aber R C. Dermatitis from cashew nuts. *J Am Acad Dermatol* 1984:10:627-31.
2. Burks A W, James J M, Hiegel A, Wilson G, Wheeler J G, Jones S M, Zuerlein N. Atopic dermatitis and food hypersensitivity reactions. *J Pediatr* 1998; 132:132-6.
3. Tariq S M, Stevens M, Matthews S, Ridout S, Twiselton R, Hide D W. Cohort study of peanut and tree nut sensitization by age of 4 years. *BMJ* 1996; 313:514-7.
4. Garcia F, Moneo I, Fernandez B, Garcia-Menaya J M, Blanco J, Juste S, Gonzalo J. Allergy to Anacardiaceae: description of cashew and pistachio nut allergens. *J Investig Allergol Clin Immunol* 2000; 10; 173-7.
5. Fernandez C. Fiandor A, Martinez-Garate A, Martinez Quesada J. Allergy to pistachio: crossreactivity between pistachio nut and other Anacardiaceae. *Clin Exp Allergy* 1995; 25:1254-9.
6. Parra F M, Cuevas M, Lezaun A, Alonso M D, Beristain A M, Losada E. Pistachio nut hypersensitivity: identification of pistachio nut allergens. *Clin Exp Allergy* 1993; 23:996-1001.
7. Burks A W, Shin D. Cockrell G. Stanley J S, Helm R M, Bannon G A. Mapping and mutational analysis of the IgE-binding epitopes on Ara h 1, a legume vicilin protein and a major allergen in peanut hypersensitivity. *Eur J Biochem* 1997; 15; 245:334-9.
8. Chomczynski P., Sacchi N. Single step method of RNA isolation by acid guanidinium thiocyanate-phenol-chloroform extraction. *Anal Biochem* 1987; 162:156-9.
9. Sze-Tao K W C, Schrimpf J., Teuber S S, Roux K H, Sathe S K. Effects of processing and storage on walnut (*Juglans regia* L.) tannins. *J Sci Food Agric* 2001; 81:1215-22.
10. Robotham J M. Teuber S S, Sathe S K. Roux K H Linear IgE epitope mapping of the English walnut (*Juglans regia*) major food allergen, Jug r 1. *J Allergy Clin Immunol* 2002: 109: 143-9.
11. Marcus J P, Green J L, Goulter K C, Manners J M. A family of antimicrobial peptides is produced by processing of a 7S globulin protein in *Macadamia integrifolia* kernels. *Plant J.* 1991; 19:699-710
12. Belanger F C, Kriz A L. Molecular basis for allelic polymorphism of the maize Globulin-1 gene. *Genetics* 1991; 129:863-72
13. Belanger F C. Kriz A L. Molecular characterization of the major maize embryo globulin encoded by the Glb1 gene. *Plant Physiol.* 1989; 91:636-43.
14. Grimes H D, Overvoorde P J, Ripp K, Franceschi V R, Hitz W D. A 62-kD sucrose binding protein is expressed and localized in tissues actively engaged in sucrose transport. *Plant Cell.* 1992; 4:1561-74.
15. Teuber S S, Jarvis K C, Dandekar A M, Peterson W R, Ansari A A. Cloning and sequencing of a gene encoding a vicilin-like protein, Jug r 2, from English walnut kernel (*Juglans regia*): a major food allergen. *J Allergy Clin Immunol* 1999; 104:1311-20.
16. Rabjohn P, Helm E M. Stanley J S, West C M, Sampson H A. Burks A W, Bannon G A. Molecular cloning and epitope analysis of the peanut allergen Are h 3. *J Clin Invest.* 1999; 103:535-42.
17. Helm R M, Cockrell G, Connaughton C, West C M, Herman E, Sampson H A, Bannon G A, Burks A W. Mutational analysis of the IgE-binding epitopes of P34/Gly m Bd 30K. *J Allergy Clin Immunol.* 2000; 105:378-84.
18. Stanley J S, King N, Burks A W, Huang S K, Sampson H. Cockrell G, Helm R M. West C M , Bannon G A. Identification and mutational analysis of the immunodominant IgE binding epitopes of the major peanut allergen Ara h 2. *Arch Biochem Biophys* 1997; 342:244-53.

19. Beezhold D H, Hickey V L, Sussman G L. Mutational analysis of the IgE epitopes in the latex allergen Hey b 5. *J Allergy Clin Immunol.* 2001; 107:1069-76.
20. Heiss S, Mahler V, Steiner R, Spitzauer S, Schweiger C. Kraft D. Valenta R. Component-resolved diagnosis (CRD) of type I allergy with recombinant grass and tree pollen allergens by skin testing. *J Invest Dermatol.* 1999; 113: 830-7.
21. Valenta R, Vrtala S, Focke-Tejkl M, Bugajska-Schretter, Ball T, Twardosz A, Spitzauer S, Gronlund H, Kraft D. Genetically engineered and synthetic allergen derivatives: candidates for vaccination against type I allergy. *Biol Chem* 1999; 380:815-24
22. Bannon G A, Cockrell G, Connaughton C, West C M, Helm R. Stanley J S, King N, Rabjohn P. Sampson H A, Burks A W. Engineering, characterization and in vitro efficacy of the major peanut allergens for use in immunotherapy. *Int Arch Allergy Immunol* 2001; 124; 70-2.
23. Niederberger V, Stubner P, Spitzauer S, Kraft D, Valenta R, Ehrenberger K, Horak F. Skin test results but not serology reflect immediate type respiratory sensitivity: a study performed with recombinant allergen molecules. *J Invest Dermatol.* 2001:117:848-51.
24. Bhalla P L, Swoboda I, Singh M B. Reduction in allergenicity of grass pollen by genetic engineering. *Int Arch Allergy Immunol* 2001; 124:51-4.
25. Nordlee J A, Taylor S L, Townsend J A, Thomas L A, Bush R K. Identification of a Brazil-nut allergen in transgenic soybeans. *New Engl J Med* 1996; 334:688-92.
26. Maleki S J, Kopper R A, Shin D S, Park C W. Compadre C M. Sampson H, Burks A W, Bannon G A. Structure of the major peanut allergen Ara h 1 may protect IgE-binding epitopes from degradation. *J Immunol* 2000; 164:5844-9
27. van Kampen V, Becker W M, Chen Z, Rihs H P, Mazur G, Raulf M, Liebers V, Isringhausen-Bley S, Baur X. Analysis of B-cell epitopes in the N-terminal region of Chi t I component III using monoclonal antibodies. *Mol Immunol.* 1994; 31:1133-40.
28. Breiteneder H, Ferreira F, Reikerstorfer A, Duchene M, Valenta R, Hoffmann-Sommergruber K. Ebner C, Breitenbach M, Kraft D, Scheiner O. Complementary DNA cloning and expression in *Escherichia coli* of Aln g I, the major allergen in pollen of alder (*Alnus glutinosa*). *J Allergy Clin Immunol.* 1992; 90:909-17.
29. Ball G, Shelton M J, Walsh B J, Hill D J, Hosking C S, Howden M E. A major continuous allergenic epitope of bovine beta-lactoglobulin recognized by human IgE binding. *Clin Exp Allergy.* 1994; 24:758-64.
30. Aas K, Elsayed S. Physico-chemical properties and specific activity of a purified allergen (codfish). *Dev Biol Stand* 1975; 29:90-8.
31. Elsayed S, Holen E, Dybendal T. Synthetic allergenic epitopes from the amino-terminal regions of the major allergens of hazel and birch pollen. *Int Arch Allergy Appl Immunol.* 1989:89:410-5.
32. Herian A M, Taylor S L, Bush R K. Identification of soybean allergens by immunoblotting with sera from soy-allergic adults. *Int Arch Allergy Appl Immunol.* 1990; 92:193-8.
33. Shanti K N, Martin B M, Nagpal S, Metcalfe D D, Rao P V. Identification of tropomyosin as the major shrimp allergen and characterization of its IgE-binding epitopes. *J Immunol* 1993; 151:5354-63.
34. Schramm G, Bufe A, Petersen A, Haas H, Merget R. Schlaak M, Becker W M Discontinuous IgE-binding epitopes contain multiple continuous epitope regions: results of an epitope mapping on recombinant Hol I 5, a major allergen from velvet grass pollen. *Clin Exp Allergy.* 2001; 31:331-41.
35. Vila, L., Beyer K, Jarvinen K M, Chatchatee P, Bardina, L, Sampson HA. Role of conformational and linear epitopes in the achievement of tolerance in cow's milk allergy. *Clin Exp Allergy* 2001; 31:1599-1606.
36. Bredehorst R, David K. What establishes a protein as an allergen? *J Chrom B* 2001; 756:33-40.
37. Sicherer, S H, Furlong T J, Munoz-Furlong A. Burks A W. Sampson H A. A voluntary registry for peanut and tree nut allergy: Characteristics of the first 5149 registrants. *J Allergy Clin Immunol* 2001; 108:128-32.
38. Pelikan Z. The diagnostic approach to immediate hypersensitivity in patients with allergic rhinitis; a comparison of nasal challenges and serum RAST. *Ann Allergy* 1983; 51:395-400.
39. Bousquet J. Lebel B, Dhivert H, Bataille Y, Martinot B, Michel F B. Nasal challenge with pollen grains, skin-prick tests and specific IgE in patients with grass pollen allergy. *Clin Allergy* 1987; 17:529-36
40. Rasanen L, Kuusisto P. Penttila M, Nieminen M, Savolainen J, Lehto M. Comparison of immunologic tests in the diagnosis of occupational asthma and rhinitis. *Allergy.* 1994; 49:342-7,

SUMMARY OF THE INVENTION

With the foregoing in mind, the present invention advantageously provides purified linear epitope polypeptide sequences from cashews, nucleic acid sequences encoding therefor, and associated methods employing the discovered sequences.

There has been considerable interest in recent years in precise biochemical and immunological characterization of allergens for possible application to immunotherapy, clinical screening and immunoassay development.[18-21] Moreover, new advances in plant genetic engineering may allow the for the alteration of plant proteins to generate hypoallergenic cultivars.[22] Not only is it important to identify allergens for possible modification in host plants but there is a need for information on the potential for allergenicity of the products of genes that are to be transferred to unrelated hosts for nutritional, processing or management purposes as witnessed by the ill-fated attempt to transfer Brazil nut 2S albumin genes to certain crops.[23] It is thus important that as many food allergens as possible, both major and minor, be identified to add to this database of information.

An invaluable method for allergen identification relies on the screening of cDNA libraries produced from the offending tissue and screened with allergen-specific antibody. We have applied this approach to the identification of the precursor of a cashew allergen designated Ana o 1, another allergen of the vicilin-like protein family. The 7S globulins from legumes are referred to as vicilins and are seed storage proteins which often exist as large trimeric oligomers in the seed protein bodies with individual subunits usually 40-70 kDa in size. Peanut vicilin, Ara h 1, has been shown to resist proteolysis when in a trimeric configuration, a property which may contribute to its allergenicity.[24] Globulin proteins from several non-leguminous plant seeds have been found to have significant sequence homology to the vicilins and can thus be designated as part of the vicilin group of proteins (vicilin-like), such as the previously described walnut (*Juglans regia*) tree nut allergen, Jug r 2.[13]

The unique IgE-binding patterns of each pool of sera to the Ana o 1 epitopes suggests a heterogeneity of recognition patterns between patients though some peptides were recognized by members of two or all three pools. Perhaps significantly, the most strongly reacting peptides were the three recognized by the sera in all three pools with the exception of epitope #6 which was strongly recognized only by pool one.

Multiple linear IgE-binding epitopes residing on one allergenic peptide have been observed in many other cases of foods known to cause immediate hypersensitivity reactions [25-31] though we recently reported finding only a single linear epitope on the walnut 2S albumin, Jug r 1.[10] The fact that most allergens have multiple IgE-binding sites is at least partly due to the polyclonal nature of the immune response to these allergens.[16]

When considered together, conformational and linear epitopes may cover the entire surface of some allergens (i.e., Hol h 1 grass allergen).[32] Interestingly, the linear epitopes rather than the conformational epitopes have been reported to be better predictors of allergy persistence as in cow's milk allergy.[33]

To date, no common structural characteristics of linear-IgE epitopes have been identified (reviewed in[34]), but this could change as more epitope mapping studies are completed. Cashew Ana o 1 and the major allergen in peanuts, Ara h 1, are both vicilins and both express multiple epitopes, in fact, 23 linear epitopes have been described for Ara h 1.[7] In parallel with the observations on Ara h 1, we did not observe any obvious sequence motifs that are shared by any two linear epitopes within the Ana o 1. Surprisingly, even though these two proteins share 27% identity and 45% similarity in amino acid sequence and presumably are similar in overall structure, there was no significant sequence conservation between epitopes of the two allergens. Moreover, even though three epitopes toward the C-terminal end of the compared sequences showed positional overlap, most of the rest did not. Though it is still possible that conformational (discontinuous) epitopes could be shared in common, these remarkable observation may help explain the lack of crossreactivity between tree nut and peanut reactive patients' sera[35].

Based on our previous immunoblotting of cashew proteins, it is known that major allergens are located in the 2S albumin protein family and the legumin family. Interestingly, our cDNA library constructed late in maturation appears to have overwhelmingly contained mRNA for the vicilin-like storage protein. This protein is a major allergen by definition (bound by $\geq$50% of allergic patients). Since several studies have shown that there is no direct correlation between binding strength in in vitro assays and in vivo reactivity[21,36-38], the relative importance of this protein among the various cashew proteins responsible for the allergic reaction in sensitive patients is yet to be determined. Efforts are underway to clone cDNAs encoding the additional allergenic cashew seed storage proteins.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 1 shows in A the nucleotide sequences of cDNA clones of Ana o 1.0101 (Ao1.1 also SEQ ID NO:1) and Ana o 1.0102 (Ao1.2 also SEQ ID NO:2), and in B the amino acid sequences of their respective polypeptides (Ao1.1 equals SEQ ID NO:3 and Ao1.2 equals SEQ ID NO:4), according to an embodiment of the present invention; the N-terminal amino acid of the recombinant peptides, Ana o 1a and Ana o 1b, are indicated (^); the presumed allelic difference between the 2 genes is indicated in bold type; the presumed start and stop codons are underlined; asterisks denote identity: GenBank accession numbers are AF395893 and AF395894;

DETAILED DESCRIPTION OF THE PREFERRED EMBODIMENT

Figure 2:
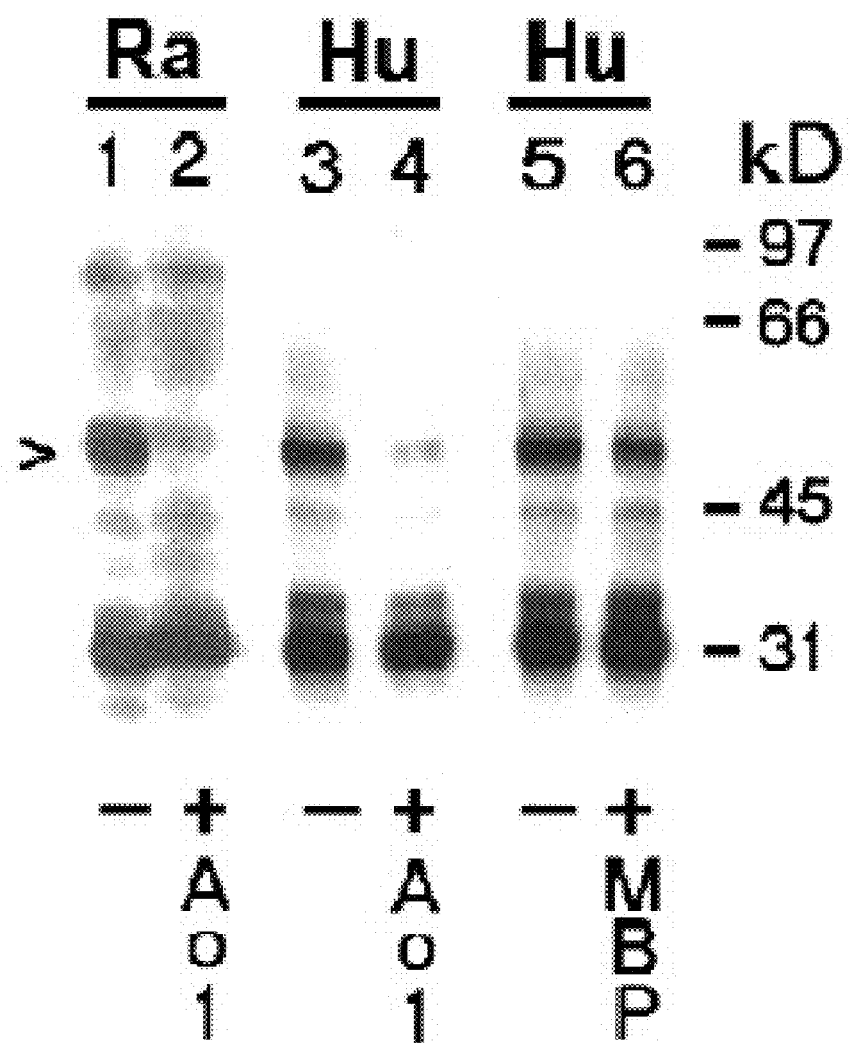
FIG. 2 shows a Western blot identification of native Ana o 1 polypeptide of the present invention; nitrocellulose blots of total cashew extract probed with rabbit anti-cashew extract antiserum (Ra) and human serum from a patient with cashew allergy (no. 9, Hu) are shown; lanes 1, 3, and 5, no inhibitor added (−); lanes 2 and 4, 5 μg of purified rAna o 1 preincubated and coincubated with anti-sera; lane 6, 5 μg of recombinant MBP preincubated and coincubated with antisera; arrow indicates inhibited band in lanes 2 and 4.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Terms Employed

List of acronyms and abbreviations used.
DTT: dithiothreitol
EDTA: ethylenediamine tetraacetic acid
HRP: horseradish peroxidase
PCR: polymerase chain reaction
PBS: phosphate buffered saline
RAST: radioallergosorbent test
SDS-PAGE: sodium dodecyl sulfate polyacrylamide gel electrophoresis
TBS: tris-buffered saline
RT: room temperature
Isolated Nucleic Acid. An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, the following:

a) a DNA whose sequence is part of a naturally occurring genomic DNA molecule but which is not associated with the coding sequences that would normally lie adjacent the sequence in the naturally occurring genome of the organism of origin;

b) a nucleic acid sequence inserted in a vector or in the genome of a prokaryotic or eukaryotic cell so as to result in a nucleic acid molecule different from a naturally occurring vector or the natural genomic DNA;

c) a discrete molecule such as a cDNA, or a fragment such as a genomic fragment, one produced by the polymerase chain reaction (PCR), or a fragment produced by a restriction enzyme; and d) a recombinant nucleotide sequence forming part of a hybrid gene, for example, a gene encoding a fusion protein. Mutation by substitution. A mutation by substitution is generally intended to mean a conservative substitution, which is the replacement of one amino acid residue with a different residue having similar biochemical characteristics, such as size, charge, and polarity vs. nonpolarity.

Methods

Human sera. Blood samples were drawn after informed consent from patients with life-threatening systemic reactions to cashew nut and the sera frozen at −70° C. until use. The study was approved by the human subjects review committee of the University of California at Davis. The presence of cashew-reactive IgE was confirmed by Pharmacia ImmunoCAP assay or by Western immunoblotting as described below. Control sera were obtained from patients with a history of anaphylaxis to walnut, pistachio or hazelnut who reported tolerance of cashews.

Cashew protein extract. An albumin/globulin extract was prepared as previously described.[7] Protein concentrations were measured by use of the Bradford protein assay (BioRad Laboratories, Inc., Hercules. CA).

Production of rabbit polyclonal antiserum. A rabbit was immunized with 5 mg of cashew extract in Freund's complete adjuvant and boosted four weeks later with 5 mg of cashew extract in incomplete Freund's adjuvant. The rabbit was subsequently bled and the serum stored at −20° C.

Construction and IgE immunoscreening of cashew cDNA library. Four cashew nuts in late maturation were chopped, frozen in liquid nitrogen, and ground with a mortar and pestle. Total RNA was extracted in TRIzol (GIBCO BRL Life Technologies Inc., Rockville, Md.) as previously described[8] and mRNA was isolated using a PolyATtract kit (Promega, Madison, Wis.) according to the manufacturer's instructions. The construction of the cDNA library was performed using the Uni-ZAP XR Gigapack Cloning Kit (Stratagene Inc., Cedar Creek, T X) following the manufacturer's instructions. The double-stranded cDNAs with EcoR I (using a 5' end adapter) and Xho I (using a 3' end PCR primer) cohesive ends were cloned into the lambda Uni-ZAP XR expression vector. The library was amplified on E. coli strain XL1-Blue. The amplified library was initially screened with rabbit anti-cashew serum at 1:5,000 dilution. Bound IgG was detected using HRP-conjugated goat anti-rabbit IgG antibody (Sigma, St. Louis, Mo.) at 1:50,000 dilution and developed with the ECL Plus chemiluminescent kit (Amersham Pharmacia Biotech Inc., Piscataway, N.J.). Clones were subsequently screened with antiserum from a cashew-allergic patient (at 1:20 dilution) and detected using HRP-conjugated goat anti-human IgE antibody (Biosource International, Camarillo, Calif.) at 1:2000 dilution and developed with ECL. The immunopositive clones were picked, plaque-purified, and stored in SM buffer supplemented with 2% chloroform at 4° C.

Sequencing and corresponding analysis of selected genes. Inserts from the selected phage clones were amplified with M13 forward and reverse primers by PCR. Both strands of the PCR products were then sequenced on an ABI 3100 Genetic Analyzer (Foster City, Calif.) using capillary electrophoresis and Version 2 Big Dye Terminators as described by the manufacturer. Similarity searches and alignments of deduced amino acid sequences were performed on Genetics Computer Group (GCG) software (Accelrys, Inc. San Diego, Calif.) using the basic local alignment search tool (BLAST) program.

Cloning, expression and purification of cDNA-encoded proteins. cDNA coding sequences were modified by the addition of an Xba I site at 5' end and an Pst I site at 3' end by PCR using Pfu Turbo DNA polymerase (Stratagene Inc. Cedar Creek, T X). followed by digestion and ligated to their respective sites of the maltose binding protein (MBP) fusion expression vector pMAL-c2 (New England BioLabs Inc., Beverly, Mass.), containing a thrombin cleavage site.

Competent E. coli BL21 (DE3) cells (Novagen Inc., Madison, Wis.) were transformed with cDNA/pMAL-c2 plasmids, and single colonies grown at 37° C. to an $OD_{600}$ of 0.5, and induced with isopropyl-D-thiogalactopyranoside (IPTG). The cells were harvested, resuspended in amylose resin column buffer (20 mM Tris-HCl; pH 7.4, 200 mM NaCl, 10 mM β-mercaptoethanol, 1 mM EDTA), lysed with mild sonication, centrifuged at 12,000 g, passed over an amylose affinity column and the fusion protein eluted with column buffer containing 10 mM maltose. Fusion proteins were cleaved with thrombin (Sigma, St. Louis, Mo.) at 1 mg of fusion protein/1 ⁿa of thrombin in column buffer (3 hr. RT). The liberated recombinant protein was purified by HPLC on a Superdex 200 column (Amersham Pharmacia, Piscataway. NJ) concentrated, and either stored (briefly) at 4° C. until use or frozen at −70° C.

Polyacrylamide gel electrophoresis (PAGE) and protein transfer. Recombinant protein or cashew extract samples were subjected to SDS-PAGE (12%) with 0.5 µg recombinant protein or 200 to 300 µg total cashew extract per 4 mm well width and used for immunoblotting as previously described.[9]

IgE Western immunoblotting and inhibitions.

Strips (3-4 mm wide) of blotted nitrocellulose which were blocked for 1 hour at RT in phosphate buffered saline (PBS)/3% nonfat dry milk/0.2% Triton X-100 (TX-100). Diluted sera (1:5 v:v in the blocking buffer, but 1:20 v:v was used for highly reactive sera) were added to the strips and incubated overnight at RT. The strips were then washed for 20 minutes three times in PBS/0.01% TX-100 and incubated overnight at RT with equine polyclonal $^{125}$I-anti-human IgE (Hycor Biomedical Inc., Garden Grove. CA) diluted 1:5 in the nonfat milk buffer. The strips were washed as above and exposed to x-ray film (Kodak X-OMAT).

For inhibition experiments, 10 ug of recombinant Ana o 1 (with and without associated MBP) were pre incubated with human or rabbit antisera. Human antiserum (from patient #9 at 1:20 dilution) or rabbit antiserum (at 1:5000 dilution) were incubated with Ana o 1 for 1 hr at 37° C. and then incubated with NC strips containing blotted cashew extract overnight at 4° C. Controls included strips incubated with human or rabbit antisera without added Ana o 1, and with normal human and rabbit serum. The strips were then washed for 15 min followed by three 5 min washes in TBS-T and incubated with goat anti-rabbit IgG-HRP (Sigma, St. Louis, Mo.) at 1:50,000 in TBS-T for 1 hr at RT or $^{125}$I anti-human IgE at 1:10 in PBS-T with 5% dried milk overnight at 4° C. The strips were washed as above and for human antibody, the reactive bands identified by exposure to x-ray film (Kodak X-OMAT) directly or, for rabbit antibody, developed using ECL-Plus chemiluminescence kit (Amersham Pharmacia Biotech, Inc, Piscataway, N.J.), as described by the manufacturer, followed by exposure to x-ray film (Kodak X-OMAT).

N-terminal amino acid sequencing. SDS-PAGE was carried out as above on reduced cashew polypeptides, using a 10% acrylamide gel, and proteins were transferred to Trans-Blot PVDF membrane (0.2 mm) (BioRad). The N-terminal sequence of the approximately 50 kD protein was determined using blotted protein on an ABI 477A sequencer with an on-line 120A HPLC system (Applied Biosystems, Inc. Foster City, Calif.). Internal tryptic digests after carboxymethylation were performed on the bands from a wet acrylamide gel, separated by ABI 173 Microbore HPLC, and then sequenced as above. Sequence data were collected utilizing ABI Procise software (Applied Biosystems, Inc.) and analyzed with FASTA programming (European Bioinformatics Institute).

Solid-phase peptide (SPOTs) synthesis and binding to IgE. Based on the derived amino acid sequence of the 540 amino acid Ana o 1 protein, 66 overlapping 15-amino acid peptides, each offset by eight amino acids, were synthesized and probed with pooled patients' sera diluted 1:5 (v:v) in Genosys blocking buffer followed by washing,) incubation with $^{125}$I-anti-human IgE (Hycor Biomedical Inc.) and 48 hr exposure at −70° C. to Kodak Biomax x-ray film as previously described.[10]

Results

Library screening and gene characterization. The initial screening included separate probings with human serum (IgE immunodetection) and rabbit antisera (IgG immunodetection). Clones that gave positive signals for both probes were selected, as one of our future goals is to determine the degree of epitope overlap between these two species. A total of 50 clones were selected of which four were purified and sequenced. The four clones varied in length from 1699 to 1781 nt, excluding the poly-A tails. Comparison of the sequences revealed that three differed only in the length of their 3' ends. A forth shared a common 3' end but its 5' end was truncated and fused via an adapter sequence with another apparently unrelated cDNA sequence showing homology with plant ABA-responsive protein (data not shown). Gene Ao1.1 (shown in FIG. 1A) represents the longest version of the cDNAs and Ao1.2 is the truncated version. Note that only a single nucleotide substitution (A for G) at residue 994 distinguishes Ao1.1 and Ao1.2 in their region of common overlap suggesting that this represents an allelic difference. Protein sequence characterization. Analysis of the deduced amino acid sequence revealed a 540 aa open reading frame, a possible start codon at position 3, and possible leader peptide from 3 to 28 (FIG. 1B). Probing of the selected clones by PCR using an internal (Ao1-specific) primer paired with a vector primer to amplify the 3' ends of the cDNA inserts revealed that all but two of the remaining 46 plaques were Ao1-like and each produced an amplicon similar in size to Ao1 (data not shown).

A search of Genbank revealed that Ao1.1 and Ao1.2 encode members of the 7S (vicilin) superfamily of proteins. Sequences with the highest aa identity and similarity were in the 33% to 43% and 52% to 62% range, respectively, and were variously described as vicilins and sucrose-binding proteins and their precursors, and 7S globulins from nut and seed crops (Table 1).[11-13]

Reactivity of the recombinant protein with human IgE and rabbit IgG. For immunological characterization, we cloned a long version of the Ao1.1 cDNA (designated Ao1.1a) beginning (at K29) after the presumptive leader peptide, and a short version (Ao1.1b), beginning with the methionine residue 102 (M102) (FIG. 1B). The DNA segments were ligated into an expression vector designed to allow for purification of the recombinant molecules by way of a mannose-binding protein fusion domain in conjunction with an amylose affinity column and a thrombin-specific cleavage site. The resulting ~105 kD, and ~93 kD fusion proteins Ana o 1a and b, respectively, were affinity purified and digested with thrombin to yield ~65 and ~55 kD peptides, respectively, as well as the 43 kD MBP. Both cleaved and uncleaved peptides were reactive with specific human IgE and rabbit IgG.

Recognition of Ana o 1 as an allergen. The prevalence of reactivity to rAna o 1 among cashew allergic patients by Western immunoblotting is shown in Table II. IgE from 10 of 20 sera from patients with a history of life-threatening reactions to cashews bound the recombinant. In four cases, the intensity of the signal was strong, but was weak in seven cases, implying though not proving, variable titers of antibody directed to this protein. In contrast, 2 of 8 sera from patients tolerant of cashew but clinically with life-threatening reactions to other tree nuts reacted with the rAna o 1. One of these (#22) showed weak binding (the patient self-reported mild throat scratchiness with cashew) while the other (#21) showed strong binding yet the patient reconfirmed no symptoms upon cashew ingestion but has had four emergency department visits after accidental walnut or pecan ingestion, and recent strong wheals and flare reaction to walnut and cashew upon skin prick testing.

Identification of native Ana o 1 by SDS-PAGE immunoblotting. To identify the band or bands in a typical total cashew immunoblot that correspond to the cloned polypeptide storage protein precursor we attempted to inhibit the binding of sera from a cashew extract-immunized rabbit and allergic patient #9 to nitrocellulose strips blotted with total soluble cashew extract using purified rAna o 1 as the inhibitor (FIG. 2). No inhibitor was added to the antisera used to probe the left strip in each pair (lanes 1, 3 and 5) whereas the antisera used to probe the right strip in each pair (lanes 2 and 4) was pre- and co-incubated with 5 ug of purified rAna o 1 protein. Serum used in lane six was pre- and co-incubated with 5 ug of rMBP. It can be seen that recombinant protein inhibits IgE binding to a band of molecular mass ~50 kD. Similar results were seen when undigested rAna o 1/MBP was used as the inhibitor (data not shown). Thus, the native precursor, corresponding to our ~65 kD recombinant protein, appears to undergo further cleavage as in other vicilin group proteins.

Identification of native Ana o 1 by sequencing. N-terminal sequencing of the band identified the immunoblot inhibition was uninformative, however, one of the internal tryptic digest peptide showed 100% homology with the translated aa sequence of Ana o 1 from position 295 to 306 of SEQ ID NO:3, AFSWEILEAALK.

Identification and recognition of IgE-reactive linear epitopes on Ana o 1 and comparison to peanut vicilin linear epitopes. The entire amino acid length of Ana o 1 was studied by probing overlapping solid phase synthetic peptides with sera from 12 patients randomly assigned to three pools. Collectively, the three pools reacted with 11 linear IgE-binding epitopes which were distributed throughout the length of the protein (Table III). Three of the identified epitopes were bound by patients' sera from all three pools. Epitope #4 was bound strongly by pools 1 and 2, and moderately by pool 3. Epitope #11 was bound strongly by pool 2, but only moderately by pools 1 and 3. The third epitope, # 1, was bound moderately by all three pools. Some epitopes gave moderate (#'s 2, 3, 7, 8, 9, 10) or strong (#6) signals only when probed with pool 1. Similarly, epitope # 5 was moderately recognized only by pool 2.

Figure 3:
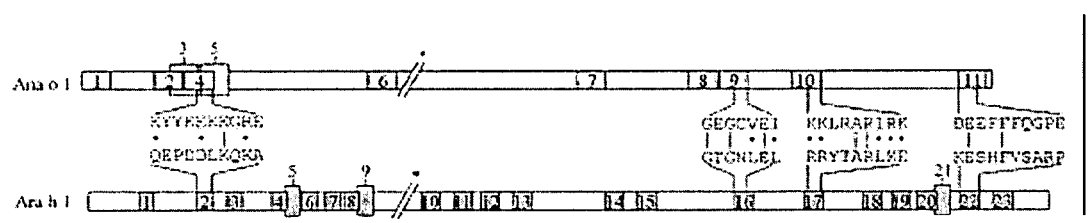
FIG. 3 compares linear epitope maps of cashew Ana o 1 with peanut Ara h 1[7]; epitopes are numbered in the figure and correspond sequentially from epitope 1 (SEQ ID NO:5) to epitope 11 (SEQ ID NO:15); larger boxes depict epitopes that overlap within a sequence. Sequences of epitopes showing positional overlap between Ana o 1 and Ara h 1 are shown for comparison; asterisks indicate breaks in sequence bars corresponding to 132-amino-acid epitope-free regions in each sequence; I, indicates identical amino acids; and •, indicates similar amino acids.

To compare the recognized linear epitopes of cashew vicilin (Ana o 1) to those of peanut vicilin (Ara h 1)[7] we aligned the two sequences using the BLAST program and highlighted the corresponding linear epitopes (diagramed in FIG. 3). Of the regions that were included in the BLAST alignment (1-528 of 540 amino acids for Ana o 1 and 1-587 of 626 for Are h 1), only four of the 11 Ana o 1 and 23 Are h I linear epitopes showed significant ($\geq 7$ amino acids) positional overlap. Even among the overlapping epitopes there was no significant homology or similarity between the Ana o1 and Are h 1 sequences considering that a single amino acid substitution usually eliminates reactivity in allergens.[7,10,14-17]

The Various Aspects of the Claimed Invention

The present invention discloses isolated nucleic acid sequences, polypeptide products thereof, and associated methods. The skilled will recognize that the isolated nucleic acids will be useful at least when expressed in a suitable cell or organism to produce the encoded polypeptides, which in turn may be employed in testing to identify patients allergic to cashew nuts. Furthermore, expression of the nucleic acid sequences of the present invention in a suitable cell may be useful in studying and characterizing gene function.

Accordingly, the present invention includes an isolated nucleic acid sequence comprising the nucleotide sequence of SEQ ID NO:1, or a degenerate variant of SEQ ID NO:1. The nucleic acid sequence described may also comprise at least one mutation selected from a deletion, a substitution, and an addition. A preferred embodiment of the invention includes an expression vector comprising the nucleic acid sequence noted above operably linked to an expression control sequence, and a cultured cell comprising this vector, the cell, or a progeny of the cell, preferably being transfected with the vector, wherein the cell expresses a polypeptide encoded by said nucleic acid sequence. Conversely, the invention further includes an isolated nucleic acid comprising a sequence that encodes a polypeptide comprising the amino acid sequence of SEQ ID NO:3.

An additional aspect of the invention includes a method of producing a protein, comprising culturing the cell comprising nucleic acid sequence SEQ ID NO:1 under conditions permitting expression of a polypeptide encoded by the nucleic acid. The method may also include purifying the polypeptide from the cell or the medium of the cell.

As noted above for SEQ ID NO:1, the invention also includes an isolated nucleic acid sequence comprising the nucleotide sequence of SEQ ID NO:2, or a degenerate variant of SEQ ID NO:2. The nucleic acid sequence described may also comprise at least one mutation selected from a deletion, a substitution, and an addition. A preferred embodiment of the invention includes an expression vector comprising the nucleic acid sequence SEQ ID NO:2 operably linked to an expression control sequence, and a cultured cell comprising this vector, the cell, or a progeny of the cell, preferably being transfected with the vector, wherein the cell expresses a polypeptide encoded by said nucleic acid sequence. Conversely, this embodiment of the invention further includes an isolated nucleic acid comprising a sequence that encodes a polypeptide comprising the amino acid sequence of SEQ ID NO:4.

Yet another method aspect of the invention includes a method of producing a protein, comprising culturing the cell comprising SEQ ID NO:2, or a degenerate variant thereof, under conditions permitting expression of a polypeptide encoded by said nucleic acid. As previously noted, the method may also include purifying the polypeptide from the cell or the medium of the cell.

The invention also discloses eleven (11) linear polypeptide epitopes, as listed in Table III, which are also respectively listed herein as SEQ ID NO:5 through SEQ ID NO:15. Accordingly, the invention includes an isolated nucleic acid comprising a sequence that encodes a polypeptide comprising an amino acid sequence selected from SEQ ID NOS:5-15. Additionally claimed is a purified Ig-E binding immunogenic polypeptide the amino acid sequence of which comprises at least one sequence selected from SEQ ID NOS:3-15, and wherein the polypeptide comprises at least one mutation in said selected amino acid sequence, the mutation being selected from a deletion, a substitution, an addition, and particularly a mutation which reduces the polypeptide's IgE-binding capacity but retains at least some immunogenicity. Those skilled in the art should recognize that the scope of the invention includes an isolated nucleic acid sequence or a degenerate variant thereof, which encodes a polypeptide consisting essentially of an amino acid sequence selected from SEQ ID NOS:3-15, and that the selected amino acid sequence may include at least one mutation such as a deletion, a substitution, or an addition. It should be understood that by "essentially" it is meant that the polypeptide is largely, but not wholly, the specified sequence.

Further method aspects of the disclosed invention include a test for detecting a cashew allergy in a patient, said test comprising contacting the patient with an amount of a purified polypeptide comprising at least one amino acid sequence selected from SEQ ID NOS:3-15. In this test, contacting preferably comprises injecting the patient with the purified polypeptide. The skilled will know that injecting includes any of the known routes useful in immunological testing of patients, for example, intradermally, and subcutaneously. Additionally, the purified polypeptide for use in such a test may comprise at least one mutation in said amino acid sequence, and the mutation may be selected from a deletion, a substitution, and an addition.

Yet a further diagnostic test of the invention for detecting anti-cashew IgE in a patient to thereby indicate an allergy to cashews, the test comprising several steps. The patient's serum is reacted with a purified polypeptide the amino acid sequence of which comprises at least one sequence selected from SEQ ID NOS:3-15. The polypeptide is separated from unreacted patient serum, and the polypeptide is reacted with a labeled human IgE-reactive agent after separating from unreacted patient serum. The polypeptide is then separated from unreacted labeled human IgE-reactive agent, and the labeled human IgE-reactive agent bound to the polypeptide after separating from unreacted agent is detected directly or indirectly to thereby indicate presence in the patient's serum of anti-cashew IgE. The amino acid sequence of the polypeptide for use in this test may also comprise at least one mutation selected from a deletion, a substitution, and an addition.

A test for screening patients for allergy to cashews may be embodied in a test kit comprising a first reagent containing at least one purified polypeptide whose amino acid sequence comprises at least one sequence selected from SEQ ID NOS: 3-15. The test kit preferably also includes a second reagent 3u containing at least one labeled human IgE-reactive agent. Additionally, in the test kit the first reagent may include a solid phase carrying the purified polypeptide.

The skilled will find additional guidance in carrying out the invention by consulting Sambrook et al., 1989, Molecular Cloning, A Laboratory Manual, Cold Spring Harbor Press, N.Y., and also Ausubel et al. (eds.), 1995, Current Protocols in Molecular Biology (John Wiley & Sons, N.Y.). In addition, guidance in diagnostic and screening test methods suitable for use with the polypeptides of the present invention may be found in Manual of Clinical Laboratory Immunology, Sixth Edition, Rose et al. (eds.), 2002. American Society for Microbiology, Washington, D.C. These publications are incorporated herein in their entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however that various modifications and changes can be made within the spirit and scope of the invention as described in the foregoing specification and as defined in the appended claims.

That which is claimed:

1. A diagnostic test for detecting anti-cashew IgE in a patient to thereby indicate an allergy to cashews, said test comprising:

reacting patient's serum with a composition comprising at least one purified polypeptide sequence selected from the group consisting of SEQ ID NOS: 5-13 and 15;

separating the polypeptide from unreacted patient serum;

reacting the polypeptide with a labeled human IgE-reactive agent after separating from unreacted patient serum;

separating the polypeptide from unreacted labeled human IgE-reactive agent; and directly or indirectly detecting the labeled human IgE-reactive agent bound to the polypeptide after separating from unreacted agent to thereby indicate presence in the patient's serum of anti-cashew IgE.

* * * * *